United States Patent [19]

Shober et al.

[11] Patent Number: 5,916,580

[45] Date of Patent: *Jun. 29, 1999

[54] METHOD OF PEST CONTROL

[75] Inventors: Edward Wharton Shober; Sandra Metcalf Shober, both of Malmesbury, United Kingdom

[73] Assignee: Demite Limited, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,497

[22] PCT Filed: Mar. 20, 1996

[86] PCT No.: PCT/GB96/00672

§ 371 Date: Jan. 9, 1997

§ 102(e) Date: Jan. 9, 1997

[87] PCT Pub. No.: WO96/28974

PCT Pub. Date: Sep. 26, 1996

[30] Foreign Application Priority Data

Mar. 21, 1995 [GB] United Kingdom .................. 9505653

[51] Int. Cl.⁶ .............................. A01N 25/00; A01N 25/34

[52] U.S. Cl. ........................... 424/405; 424/403; 8/115.7; 8/532; 8/922

[58] Field of Search ..................... 424/405, 403; 8/115.7, 532, 922; 239/6.84

[56] References Cited

U.S. PATENT DOCUMENTS 5,198,287   3/1993   Samson et al. ......................... 428/248

FOREIGN PATENT DOCUMENTS 3220102   9/1991   Japan .

OTHER PUBLICATIONS

Lindsay et al, 1991, Pestic. Sci., vol. 32, pp. 397–411.

Primary Examiner—Lynette F. Smith
Assistant Examiner—Ali R. Salimi
Attorney, Agent, or Firm—Breiner & Breiner

[57] ABSTRACT

Method of controlling dust mites involving impregnating pre-formed netting with a liquid composition including a pyrethroid insecticide is described. The netting is applied around an article, such as a pillow, mattress, duvet, cushion, beanbag or domestic pet bed.

4 Claims, 2 Drawing Sheets

METHOD OF PEST CONTROL

This is a rule 371 application based on the priorty date of PCT/GB96/00672 filed Mar. 20, 1996, which claims priority under British Application No. 9505653.7 filed Mar. 21, 1995.

The present invention relates to the use of pesticide-impregnated linings and/or coverings to control house dust mite populations. In particular, the invention relates to pyrethroid-impregnated netting for use in covering, e.g. a mattress.

The reported growth in house dust mice populations associated with domestic environments in Europe, the Americas, China and elsewhere is causing increasing concern. With the rising number of homes remaining at a constant favourable temperature and humidity, together with changes in house cleaning methods and types of bedding over the years, the numbers and survival of such creatures have risen sharply, particularly in the households of sufferers with eczema (and ichthyosis).

House dust mites are scavengers on dead organic matter found in abundance in the home, feeding principally on the shed skin scales of humans and animals. The mites, their faeces and products, are highly antigenic as contact or aero allergens in Atopic diseases, eg eczema, asthma and allergic rhinitis. Mite allergy may trigger severe exacerbation that can be life threatening in extrinsic asthma In addition, house dust mites have, in recent years, become an increased focus of concern as many experts consider them to be instrumental in initiating clinical asthma in very young children. It is believed that repeated exposure to the allergens produced by the mites can trigger early stages of asthma which will then become established as a chronic disease affected by a large range of different allergens in the environment. Even if this direct causative action of dust mites on the initial onset of asthma proves to be incorrect, there is no doubt they cause immeasurable suffering to those with specific allergies or act as a trigger for asthma attacks.

House dust mites are to be found concentrated in many parts of the home, particularly soft furnishings, which provide a highly suitable environment. It is their association with bedding, however, which brings them into the closest and most prolonged contact with humans. Pillows, duvets and mattresses have been found not only to house large populations of house dust mites, but also copious amounts of their faeces.

In the last few years, it has become recognised that netting impregnated with synthetic pyrethroid insecticides are one of the most successful means of controlling insect borne diseases. When used as curtains or draped over doors and roof eaves, such netting can significantly reduce the numbers of insects which enter and survive inside houses. The most widespread use of such impregnated netting is, of course, for bed nets to prevent mosquitos from feeding on humans at night. Trials involving many millions of people around the world have proven this technique to be effective not only at preventing mosquitos feeding, but also at controlling the spread of diseases spread by insects, such as malaria.

There are several reasons why pyrethroid insecticides are ideal for this type of impregnated netting use.

1. They have a very low mammalian toxicity which means that they are considered relatively safe for use on or near humans. Indeed, there are several preparations available on the market which can be applied directly onto the skin or hair which contain permethrin.
2. They have a very high toxicity to insects. This means that they can be used at extremely low doses and lead to rapid knockdown and kill, often within seconds or minutes of contact.
3. They are stable compounds under normal environmental conditions, often giving excellent protection levels for six months or more.
4. Unlike numerous other classes of insecticides, there is, as yet, very limited resistance in the field to these compounds.

Pyrethroid insecticides are available as a dusting powder which is designed to be used for the elimination of house dust mites. However, this does not provide for prolonged protection against infestation, and indeed depends on the efficiency of "dusting". In addition, it might be the case that dust particles themselves will aggravate any asthmatic conditions which people coming into contact with the bedding may have.

It has now been found that effective control of house dust mite populations can be effected by using an insecticide-impregnated cover adapted to fit around bedding, a mattress, etc.

Thus, in a first aspect, the present invention provides the use of an insecticide-impregnated covering for control of house dust mites. In the present context, the term "covering" is intended to mean not only a covering per se, but also a lining, sheet, backing, inlay, interlining, film, layer, overlay or the like.

Suitably, the insecticide is a pyrethroid, for example permethrin or deltamethrin.

In one embodiment of the present invention, the covering is constructed, at least in part, of netting, and is designed to fit around an article, for example a pillow, mattress, duvet, cushion, beanbag or domestic pet bed, particularly a pillow, mattress or duvet, such that the surfaces of the article are completely covered. Alternatively, a netting covering can be constructed which only covers some of the surfaces.

Alternatively, the covering is adapted to be used for lining an article, or is used as a sheet. In this way it will find use in association with articles such as a curtain, a pelmet or a wallcovering. Use of the netting is particularly advantageous in that it reduces the amount of insecticide which has to be used to achieve impregnation, and thus protection.

In a second aspect, the invention provides an insecticide-impregnated covering for use in the control of house dust mites.

In a further aspect the present invention provides an article provided with an insecticide-impregnated covering, preferably for use in the control of house dust mites. Such articles would include pillows, mattresses, duvets and the like.

In a final aspect, the present invention provides a method of controlling house dust mites which comprises the step of bringing an article into association with an insecticide-impregnated covering as defined above. In a preferred embodiment of this aspect of the invention, an article such as a mattress, pillow, duvet or the like is enclosed, or wrapped, in such an insecticide-impregnated covering. Alternatively, the method will entail partially covering the article.

In another embodiment, the method will involve bringing a curtain lining, in the form of an insecticide-impregnated netting for example, into contact with the curtain itself.

Preferred features of each aspect apply equally to each other aspect *mutatis mutandis.*

The invention will now be described with reference to the following examples which should not be considered as in any way limiting the invention.

The examples refer to the figures.

EXAMPLE 1

Materials

Netting

Two samples of netting were supplied as follows:

Net A—100% Polyester, 196 Mesh, 100 denier.

Net B—100% Polyester, 196 Mesh, 75 denier.

Insecticides

Two samples of pyrethroid were supplied by Roussel Uclaf, Berkhampsted, Herts as follows:

1) Permethrin, 10% EC (batch 9/93).

2) Deltamethrin, 1% SC (batch 2/94).

House Dust Mites

A reference colony of the house dust mite *Dermatophagoides farinae* held at LSHTM was used in all experiments.

Methods

Impregnation of netting

Squares of netting 25 cm×25 cm were impregnated by dipping in a predetermined concentration of insecticide in a water emulsion to give a final concentration as follows:

Permethrin 0.2 $g/m^2$ a.i.

Deltamethrin 25 $mg/m^2$ a.i.

After drying for 48 hours, the nets were stored at +4° C. until required.

Mortality experiments

Figure 1:
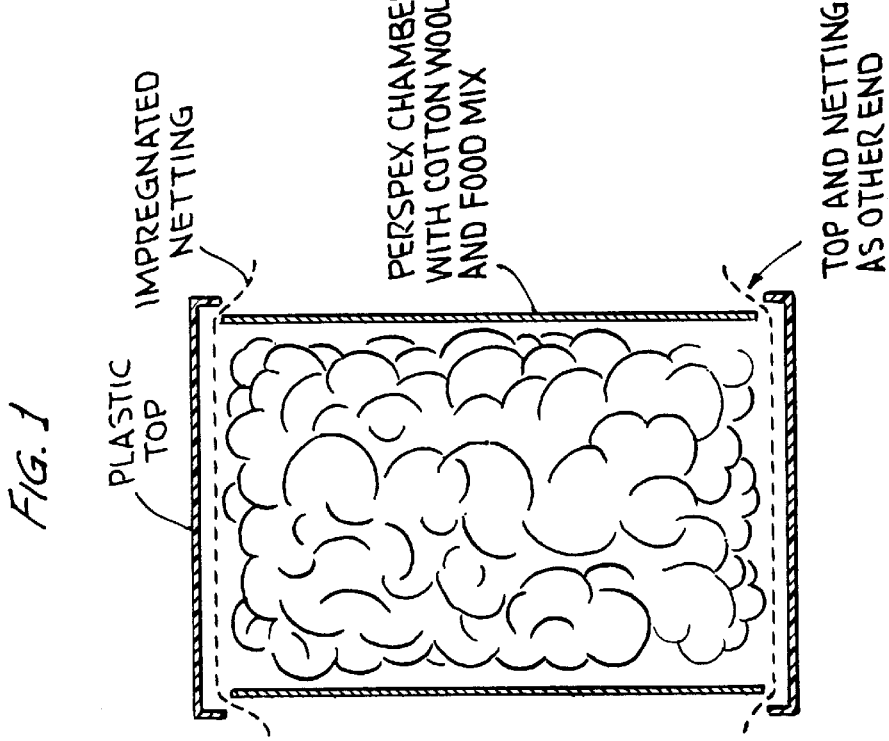
FIG. 1: shows an experimental mite holding chamber used in the investigation as described below.

In an attempt to simulate conditions which would be expected from an impregnated net mattress cover in use, a mite holding chamber was made which enabled normal habitat conditions to be maintained but with netting contact on extremities only (see FIG. 1).

The holding chamber was loosely packed with clinical grade non-absorbent cotton wool and a plentiful supply of the mites' normal laboratory food, flaked fish food. The treated or control netting was then placed over each end of the tube and held secure by a plastic lid.

A nucleus of 500+mites of mixed age and sex from the main breeding colony were transferred into each holding pot and survival/mortality recorded each week. When there were no living mites observed within the holding chamber, a further batch of mites was added and weekly observations continued.

As there are obviously inherent problems with identifying and counting such minute organisms dispersed within a relatively large holding area, a standardised technique was used on each occasion as follows:

The plastic top of one end of the chamber was removed and the contents tipped into a clean petri dish. The cotton wool matrix was studied under a microscope for a period of 10 minutes during which time the proportion of live and dead mites was recorded. The matrix was then carefully replaced and the top secured before the next chamber was checked. Although this method does not give absolute mortality figures, it does provide a constant and relatively quick way of comparing the treatment types and gauging efficacy of the impregnated netting.

Results

Figure 2:
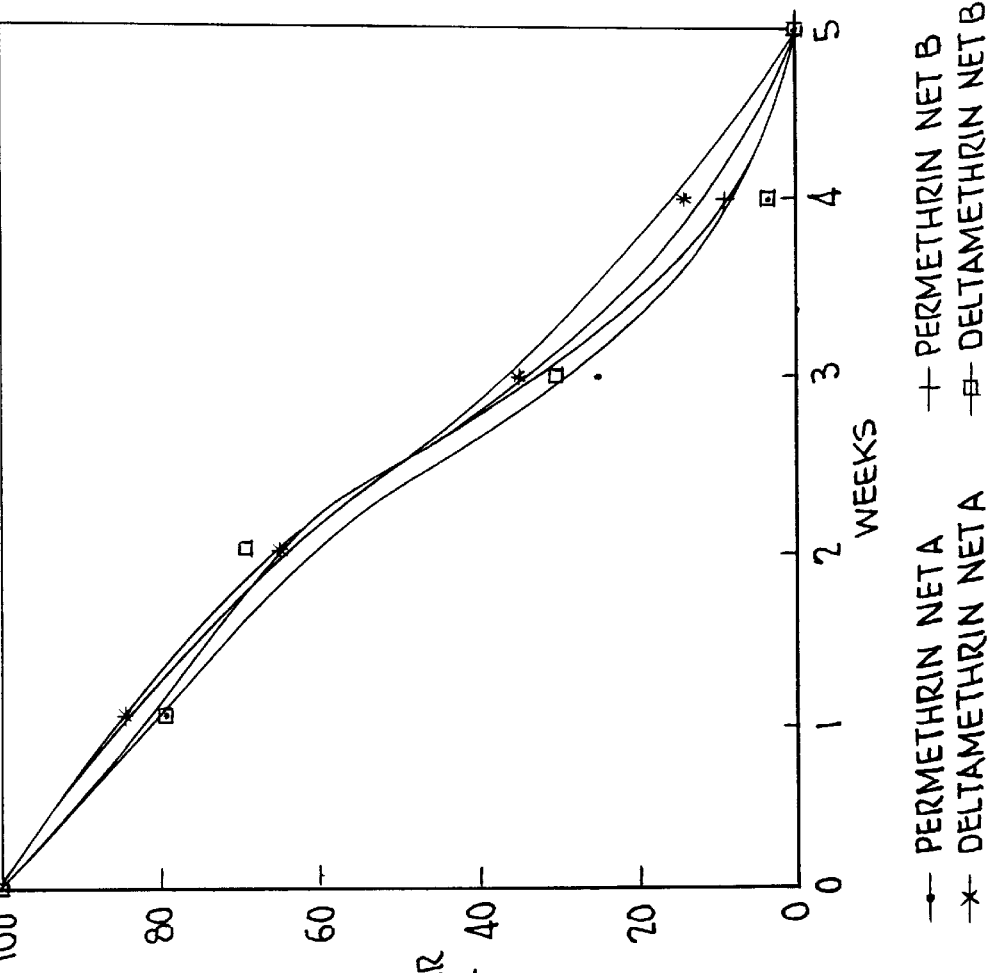
FIG. 2: shows the effects of pyrethroid netting covers on the survival of house dust mites, the netting being either impregnated with permethrin or deltamethrin.

FIG. 2 shows relative decline in living mite numbers with time. In every case there were no living mites in any treated netting chamber after 5 weeks.

When a chamber was reinfested with an additional batch of mites on week 5, and again on week 10 (see FIG. 3), there was a very rapid decline in their numbers over subsequent inspections. This clearly shows the treatment's efficacy for at least 10 weeks, and its ability to prevent reinfestation throughout this period.

Figure 3:
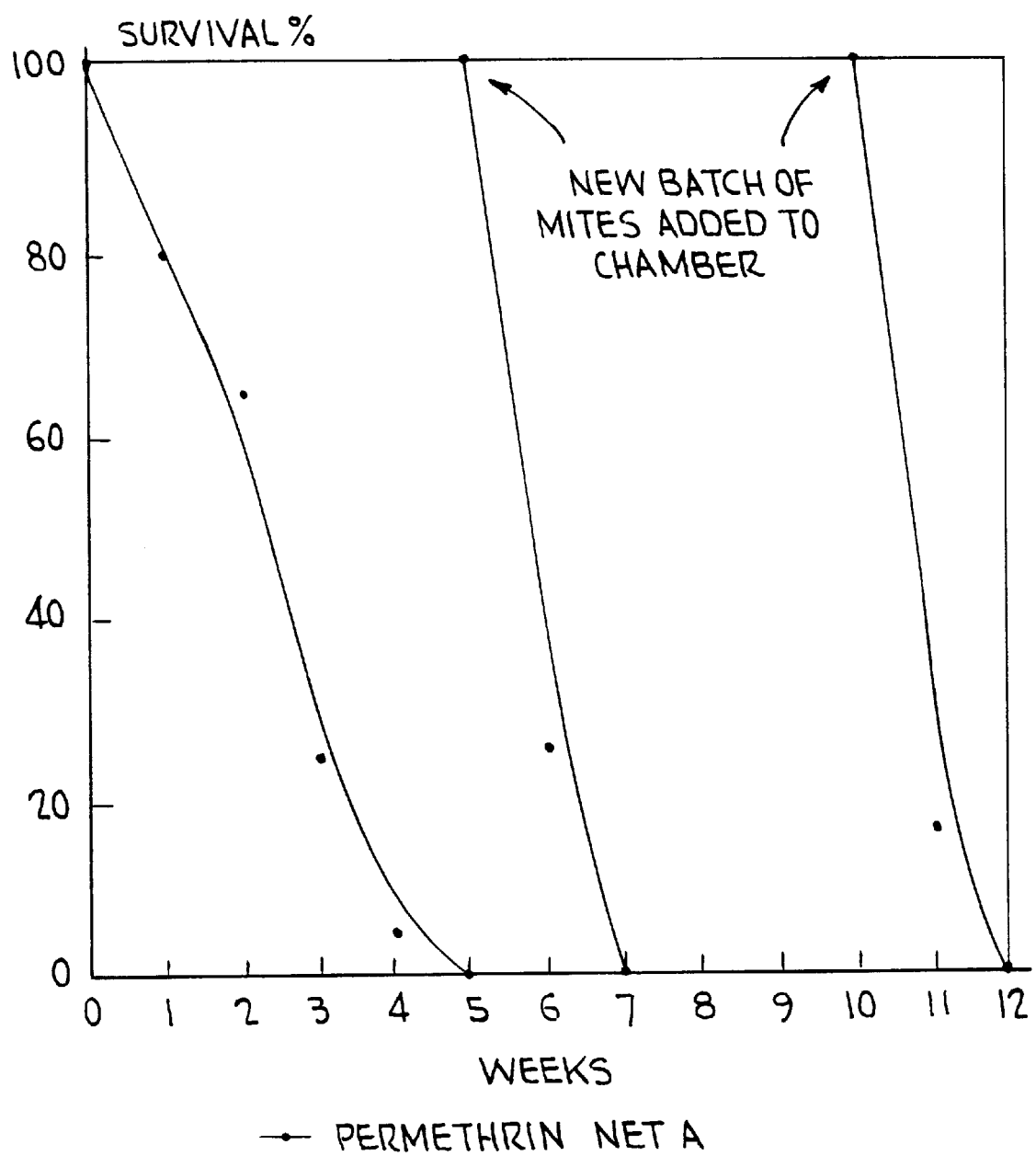
FIG. 3: shows the effects of pyrethroid netting covers on survival of house dust mites over a 12 week period, and the effect on newly introduced house mites at various time points.

FIGS. 2 and 3 show mortality studies and effects of reinfestation against time.

Discussion

Both pyrethroid insecticides gave similar levels of mortality over time. The protection period is several months at least for both insecticides and thus the choice of insecticides can be made on ease of impregnation, level of mammalian toxicity or cost.

FIG. 3 clearly indicates that the effect takes several weeks to build up in the holding matrix, but once this is achieved, it acts relatively quickly on the subsequent mite reinfestation.

These results therefore show that it is possible to reduce house dust numbers, or even eliminate enclosed populations using insecticide impregnated coverings over a prolonged period. The study shows complete mortality for periods of at least 10 weeks.

What is claimed is:

1. Method of reducing and/or eliminating a population of house dust mites using a pyrethroid insecticide comprising impregnating pre-formed netting with a liquid composition containing a pyrethroid insecticide, drying the netting, and applying the netting around a pillow, mattress, duvet, cushion, beanbag or domestic pet bed.

2. The method of claim 1 wherein the netting entirely encloses the pillow, mattress, duvet, cushion, beanbag or domestic pet bed.

3. The method of claim 1 wherein the pyrethroid is permethrin and the netting is impregnated by dipping in an aqueous emulsion containing permethrin.

4. The method of claim 1 wherein the netting is a polyester mesh.

* * * * *